(12) United States Patent
Hoffmann et al.

(10) Patent No.: US 6,806,370 B2
(45) Date of Patent: Oct. 19, 2004

(54) NK-1 RECEPTOR ACTIVE AMINE OXIDE PRODRUGS

(75) Inventors: Torsten D. Hoffmann, Weil Am Rhein (DE); Sonia Maria Poli, Basel (CH); Patrick Schnider, Oberwil (CH); Andrew Sleight, Riedisheim (FR)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 10/645,895

(22) Filed: Aug. 21, 2003

(65) Prior Publication Data

US 2004/0048901 A1 Mar. 11, 2004

Related U.S. Application Data

(62) Division of application No. 10/337,543, filed on Jan. 7, 2003, which is a division of application No. 09/904,059, filed on Jul. 12, 2001, now Pat. No. 6,593,472.

(30) Foreign Application Priority Data

Jul. 14, 2000 (EP) .............................................. 00115287

(51) Int. Cl.$^7$ ............................................ C07D 401/02
(52) U.S. Cl. ................................ 546/278.4; 546/268.4
(58) Field of Search ............................ 546/268.4, 278.4

(56) References Cited

U.S. PATENT DOCUMENTS 5,691,336 A 11/1997 Dorn et al.
5,972,938 A 10/1999 Rupniak et al.
6,297,375 B1 10/2001 Bos et al.

FOREIGN PATENT DOCUMENTS

| EP | 035 115 | 9/2000 |
|----|---------|--------|
| EP | 103 545 | 5/2001 |
| WO | WO 95/16679 | 6/1995 |
| WO | WO 95/18124 | 7/1995 |
| WO | WO 95/23798 | 9/1995 |
| WO | WO 98/04528 | * 2/1998 |

OTHER PUBLICATIONS

Hans Bundgaard, *Drugs of the Future*, vol. 16(5), pp. 443–458 (1991).
Barker, *Reviews in the Neurosciences*, vol. 7, No. 3, pp. 187–214 (1996).
Longmore et al., *Can. J. Physiol. Pharmacol.*, vol. 75, pp. 612–621 (1997).
Mark S. Kramer et al., *Science*, vol. 281, pp. 1640–1645.
Maggi et al., *J. Auton, Pharmacol*, vol. 13, pp. 23–93 (1993).
Navari et al., *The New England Journal of Medicine*, vol. 340, No. 3, pp. 190–195 (1999).
Maggi et al., *Neuropeptides*, vol. 32(1), pp. 1–49 (1998).
Doi etal., *European Journal of Pharmacology*, vol. 383(3), pp. 297–303 (1999).
Yoshinori Ikeura et al., Chem. Pharm. Bull., vol. 45(10), pp. 1642–1652 (1997).

* cited by examiner

*Primary Examiner*—Zinna Northington Davis
(74) *Attorney, Agent, or Firm*—George W. Johnston; Patricia S. Rocha-Tramaloni; Kimberly J. Prior

(57) ABSTRACT

Compounds of the invention are amine oxide prodrugs showing activity on the NK1 receptor.

13 Claims, No Drawings

NK-1 RECEPTOR ACTIVE AMINE OXIDE PRODRUGS

CONTINUITY INFORMATION

This application is a divisional of U.S. patent application Ser. No. 10/337,543, filed Jan. 7, 2003, which is a divisional of U.S. patent application Ser. No. 09/904,059, filed Jul. 12, 2001, now U.S. Pat. No. 6,593,472.

FIELD OF INVENTION

The present invention is generally related to amine oxide compounds and more particularly to amine oxide compounds and pharmaceutically acceptable salts that are antagonists of the of the Neurokinin 1 (NK-1, substance P) receptor which are prodrugs for delivery of known compounds with antagonistic activity to the Neurokinin 1 (NK-1, substance P) receptor.

BACKGROUND

A prodrug is in most cases a pharmacologically inactive derivative of a parent drug molecule that requires spontaneous or enzymatic transformation within the body in order to release the active drug, and that has improved delivery properties over the parent drug molecule. It has been shown that a molecule with optimal structural configuration and physicochemical properties for eliciting the desired therapeutic response at its target site does not necessarily possess the best molecular form and properties for its delivery to its point of ultimate action. Usually, only a minor fraction of doses administered reach the target area and since most agents interact with non-target sites as well, an inefficient delivery may result in undesirable side effects. This fact of differences in transport and in situ effect characteristics for many drug molecules is the basic reason why bioreversible chemical derivatization of drugs, i.e., prodrug formation is a means by which a substantial improvement in the overall efficacy of drugs can often be achieved. Prodrugs are designed to overcome pharmaceutically and/or pharmacokinetically based problems associated with the parent drug molecule that would otherwise limit the clinical usefulness of the drug.

In recent years several types of bioreversible derivatives have been exploited for utilization in designing prodrugs. Using esters as a prodrug type for drugs containing carboxyl or hydroxyl function is most popular. Further well-known are prodrug derivatives of peptides, 4-imidazolidinones and the like, described in *Drugs of the Future*, 1991, 16(5), 443–458 or N-oxides, described for example in U.S. Pat. No. 5,691,336.

The compounds of formula II

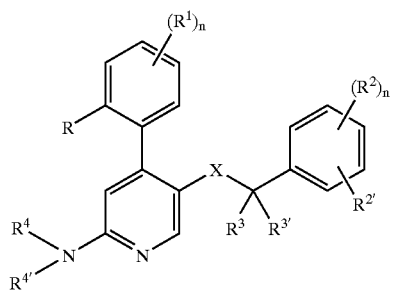

II are antagonists of the neurokinin receptor. The central and peripheral actions of the mammalian tachykinin substance P have been associated with numerous inflammatory conditions including migraine, rheumatoid arthritis, asthma, and inflammatory bowel disease as well as mediation of the emetic reflex and the modulation of central nervous system (CNS) disorders such as Parkinson's disease (Neurosci. Res., 1996, 7, 187–214), anxiety (Can. J. Phys., 1997, 75, 612–621) and depression (Science, 1998, 281, 1640–1645).

"Tachykinin Receptor and Tachykinin Receptor Antagonists", J. Auton. Pharmacol., 13, 23–93, 1993 reviews the usefulness of tachykinin receptor antagonists in pain, headache, especially migraine, Alzheimer's disease, multiple sclerosis, attenuation of morphine withdrawal, cardiovascular changes, oedema, such as oedema caused by thermal injury, chronic inflammatory diseases such as rheumatoid arthritis, asthma/bronchial hyper-reactivity and other respiratory diseases including allergic rhinitis, inflammatory diseases of the gut including ulcerative colitis and Crohn's disease, ocular injury and ocular inflammatory diseases.

Furthermore, Neurokinin 1 receptor antagonists are being developed for the treatment of a number of physiological disorders associated with an excess or imbalance of tachykinin, in particular substance P. Examples of conditions in which substance P has been implicated include disorders of the central nervous system such as anxiety, depression and psychosis (WO 95/16679, WO 95/18124 and WO 95/23798).

The neurokinin-1 receptor antagonists are further useful for the treatment of motion sickness and for treatment induced vomiting.

In addition, in The New England Journal of Medicine, Vol. 340, No. 3 190–195, 1999 describes the reduction of cisplatin-induced emesis by a selective neurokinin-1-receptor antagonist.

Further, the usefulness of neurokinin 1 receptor antagonists for the treatment of certain forms of urinary incontinence is described in Neuropeptides, 32(1), 1–49, (1998) and Eur. J. Pharmacol., 383(3), 297–303, (1999).

Furthermore, U.S. Pat. No. 5,972,938 describes a method for treating a psychoimmunologic or a psychosomatic disorder by administration of a tachykinin receptor, such as NK-1 receptor antagonist.

SUMMARY

The present invention relates to N-oxides of compounds of the formula

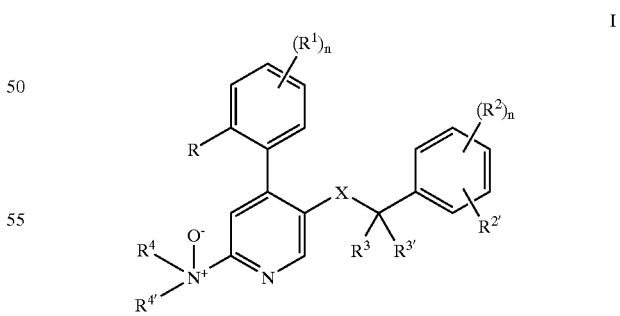

I wherein
  R is hydrogen, lower alkyl, lower alkoxy, halogen or trifluoromethyl;
  $R^1$ is hydrogen or halogen; or, when n=1, R and $R^1$, when adjacent, together can additionally bridge between the ring carbon atoms to which they are attached to form —CH=CH—CH=CH—;

$R^2$ and $R^{2'}$ are hydrogen, halogen, trifluoromethyl, lower alkoxy or cyano; or $R^2$ and $R^{2'}$ when adjacent, and when n=1, together can additionally bridge between the ring carbon atoms to which they are attached to form —CH=CH—CH=CH— unsubstituted or substituted by one or two lower alkyl or lower alkoxy;

$R^3$, $R^{3'}$ are hydrogen, lower alkyl or cycloalkyl;

$R^4$, $R^{4'}$ are —$(CH_2)_m OR^6$ or lower alkyl; or $R^4$ and $R^{4'}$ together with the N-atom to which they are attached form a 5 or 6 member nitrogen containing heterocyclic ring of the structure

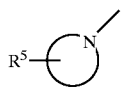

wherein said heterocyclic ring has 0 or 1 additional hetero-atoms selected the group consisting of sulfur, nitrogen and oxygen, said additional hetero-sulfur atom being a sulfide, sulfone, or sulfonyl moiety;

$R^5$ is hydrogen, hydroxy, lower alkyl, -lower alkoxy, —$(CH_2)_m OH$, —$COOR^3$, —$CON(R^3)_2$, —$N(R^3)CO$-lower alkyl or —$C(O)R^3$;

$R^6$ is hydrogen, lower alkyl or phenyl;

X is —$C(O)N(R^6)$—, —$N(R^6)C(O)$—, —$(CH_2)_m O$— or —$O(CH_2)_m$—;

n is 0, 1, 2, 3 or 4; and m is 1, 2 or 3;

and to pharmaceutically acceptable acid addition salts thereof.

It has surprisingly been found that these N-oxides of the present invention have an in vitro activity on the NK1 receptor and/or may be used as prodrugs of compounds of formula

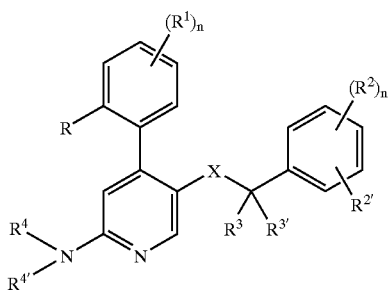

II which are antagonists of the Neurokinin 1 (NK-1, substance P) receptor.

However, the advantage of a prodrug lies in its physical properties, such as enhanced water solubility for parenteral administration compared to the parent drug, or it enhances absorption from the digestive tract, or it may enhance drug stability for long-term storage. Compounds of formula II have limited water solubility, not allowing bolus injections. It was therefore useful to find derivatives of the compound of formula II to render these compounds suitable for parenteral and intramuscular application. It has been shown that N-oxides of compounds of formula I fulfill all requirements of a good prodrug.

Objects of the present invention are the compounds of formula I and pharmaceutically acceptable salts thereof, the preparation of the above-mentioned compounds, medicaments containing them and their manufacture as well as the use of the above-mentioned compounds in the control or prevention of illnesses, especially of illnesses and disorders of the kind referred to earlier or in the manufacture of corresponding medicaments.

DETAILED DESCRIPTION

The most preferred indications in accordance with the present invention are those which include disorders of the central nervous system, for example the treatment or prevention of certain depressive disorders or emesis by the administration of NK-1 receptor antagonists. A major depressive episode has been defined as being a period of at least two weeks during which, for most of the day and nearly every day, there is either depressed mood or the loss of interest or pleasure in all, or nearly all activities.

The following definitions of the general terms used in the present description apply irrespective of whether the terms in question appear alone or in combination. As used herein, the term "lower alkyl" denotes a straight- or branched-chain alkyl group containing from 1–7 carbon atoms, for example, methyl, ethyl, propyl, isopropyl, n-butyl, i-butyl, t-butyl and the like.

Preferred lower alkyl groups are groups with 1–4 carbon atoms.

The term "lower alkoxy" denotes a group wherein the alkyl residues are as defined above, and which is attached via an oxygen atom.

The term "halogen" denotes chlorine, iodine, fluorine and bromine.

The term "cycloalkyl" denotes a saturated carbocyclic group, containing 3–6 carbon atoms.

The term "5 or 6 member nitrogen containing heterocyclic ring of the structure

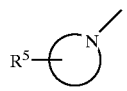

having 0 or 1 additional hetero-atoms selected from sulfur, nitrogen and oxygen, and the additional hetero-sulfur atom being a sulfonyl moiety;" denotes, for example, pyrrolidin-1-yl, piperidin-1-yl, piperazin-1-yl, morpholin-4-yl or 1,1-dioxo-thiomorpholin-4-yl, and the like.

A preferred compound of the invention of structure I includes the compound of structure

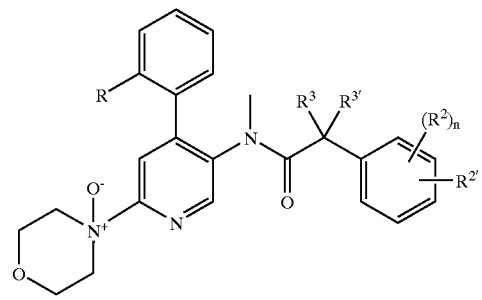

Ia wherein R, $R^3$, $R^{3'}$ and $R^2$ and $R^{2'}$ are as defined above.

Preferred compounds are those, wherein R is methyl or chloro, for example the following compounds:

2-(3,5-bis-trifluoromethyl-phenyl)-N-methyl-N-[6-(4-oxy-morpholin-4-yl)-4-o-tolyl-pyridin-3-yl]-isobutyramide,
2-(3,5-bis-trifluoromethyl-phenyl)-N-[4-(2-chloro-phenyl)-6-(4-oxy-morpholin-4-yl)-pyridin-3-yl]-N-methyl-isobutyramide,
2-(3,5-bis-trifluoromethyl-phenyl)-N-methyl-N-[6-(4-oxy-morpholin-4-yl)-4-o-tolyl-pyridin-3-yl]-acetamide,
2-(3,5-dimethoxy-phenyl)-N-methyl-N-[6-(4-oxy-morpholin-4-yl)-4-o-tolyl-pyridin-3-yl]-acetamide, or
2-(3-fluoro-5-trifluoromethyl-phenyl)-N-methyl-N-[6-(4-oxy-morpholin-4-yl)-4-o-tolyl-pyridin-3-yl]-acetamide.

Further preferred are compounds of claim 1 having the structure

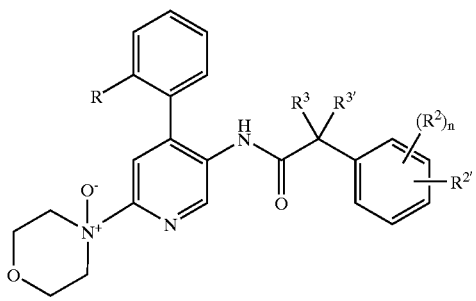

Ib wherein R, $R^2$ and $R^{2'}$, and $R^3$ and $R^{3'}$ and n are as defined above, for example the following:
2-(3,5-bis-trifluoromethyl-phenyl)-N-[6-(4-oxy-morpholin-4-yl)-4-o-tolyl-pyridin-3-yl]-isobutyramide.

Preferred are further compounds of claim 1 having the structure

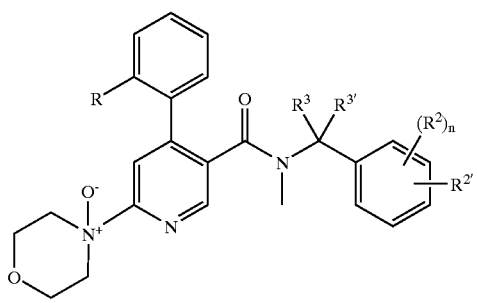

Ic wherein R, $R^2$ and $R^{2'}$, and $R^3$ and $R^{3'}$ and n are as defined above.

A preferred enbodiment of compounds of formula Ic are those, wherein R is methyl, for example the followings:

N-(3,5-bis-trifluoromethyl-benzyl)-N-methyl-6-(4-oxy-morpholin-4-yl)-4-o-tolyl-nicotinamide,
N-methyl-N-(2-methyl-naphthalen-1-ylmethyl)-6-(4-oxy-morpholin-4-yl)-4-o-tolyl-nicotinamide,
N-methyl-6-(4-oxy-morpholin-4-yl)-N-naphthalen-1-ylmethyl-4-o-tolyl-nicotinamide,
N-(2-methoxy-naphthalen-1-ylmethyl)-N-methyl-6-(4-oxy-morpholin-4-yl)-4-o-tolyl-nicotinamide,
N-(2-methoxy-benzyl)-N-methyl-6-(4-oxy-morpholin-4-yl)-4-o-tolyl-nicotinamide,
N-(5-chloro-2-methoxy-benzyl)-N-methyl-6-(4-oxy-morpholin-4-yl)-4-o-tolyl-nicotinamide,
N-(2-chloro-5-methoxy-benzyl)-N-methyl-6-morpholin-4-yl-4-o-tolyl-nicotinamide,
N-methyl-6-(4-oxy-morpholin-4-yl)-N-pentafluorophenylmethyl-4-o-tolyl-nicotinamide,
N-methyl-6-(4-oxy-morpholin-4-yl)-N-naphthalen-2-ylmethyl-4-o-tolyl-nicotinamide,
N-[2-methoxy-5-(5-trifluoromethyl-tetrazol-1-yl)-benzyl]-N-methyl-6-(4-oxy-morpholin-4-yl)-4-o-tolyl-nicotinamide or
N-(1,4-dimethoxy-naphthalen-2-ylmethyl)-N-methyl-6-(4-oxy-morpholin-4-yl)-4-o-tolyl-nicotinamide.

Preferred are further compounds having the structure

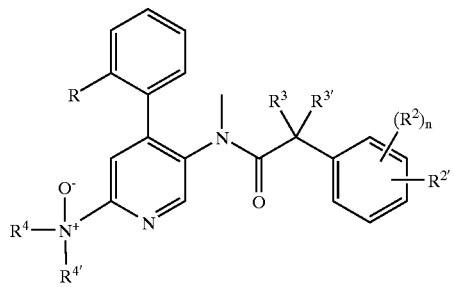

Id wherein R, $R^2$ and $R^{2'}$, $R^3$ and $R^{3'}$ and $R^4$ and $R^{4'}$ and n are as defined in claim 1.

Compounds of formula Id, wherein R is chloro, are especially preferred, for example the following compounds:

2-(3,5-bis-trifluoromethyl-phenyl)-N-[4'-(2-chloro-phenyl)-1-oxy-3,4,5,6-tetrahydro-2H-[1,2']bipyridinyl-5'-yl]-N-methyl-isobutyramide or
2-(3,5-bis-trifluoromethyl-phenyl)-N-[4-(2-chloro-phenyl)-6-oxy-dimethylamino-pyridin-3-yl]-isobutyramide.

The compounds of formula Id, wherein R is methyl, are also preferred. Such compounds are:

2-(3,5-bis-trifluoromethyl-phenyl)-N-(6-oxy-dimethylamino-4-o-tolyl-pyridin-3-yl)-N-methyl-isobutyramide,
2-(3,5-bis-trifluoromethyl-phenyl)-N-1-(4-hydroxy-1-oxy-4'-o-tolyl-3,4,5,6-tetrahydro-2H-[1,2']bipyridinyl-5'-yl)-N-methyl-isobutyramide,
2-(3,5-bis-trifluoromethyl-phenyl)-N-{6-[(2-hydroxy-ethyl)-1-oxy-methyl-amino]-4-o-tolyl-pyridin-3-yl}-N-methyl-isobutyramide or
(R)-2-(3,5-bis-trifluoromethyl-phenyl)-N-[6-(3-hydroxy-1-oxy-pyrrolidin-1-yl)-4-o-tolyl-pyridin-3-yl]-N-methyl-isobutyramide.

The compounds having the structure

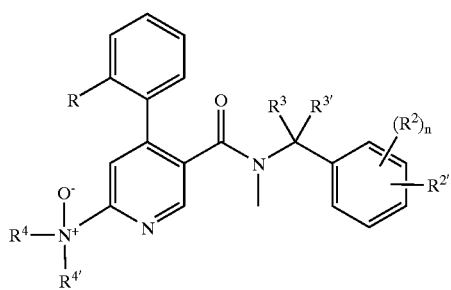

Ie are also preferred, wherein R, $R^2$, $R^{2'}$, $R^3$, $R^{3'}$ and $R^4$ and $R^{4'}$ and n are as defined above.

Examples of compounds of formula Ie, wherein R is methyl, are the followings:

4-{5-[(3,5-bis-trifluoromethyl-benzyl)-methyl-carbamoyl]-4-o-tolyl-pyridin-2-yl}-4-oxy-piperazine-1-carboxylic acid tert-butyl ester, 5'-[(3,5-bis-trifluoromethyl-benzyl)-methyl-carbamoyl]-4'-o-tolyl-1-oxy-3,4,5,6-tetrahydro-2H-[1,2']bipyridinyl-4-carboxylic acid ethyl ester, (RS)-6-[3-(acetyl-methyl-amino)-1-oxo-pyrrolidin-1-yl]-N-(3,5-bis-trifluoromethyl-benzyl)-N-methyl-4-o-tolyl-nicotinamide, N-(3,5-bis-trifluoromethyl-benzyl)-6-(1,1-dioxo-1$\lambda^{6-4}$-oxy-thiomorpholin-4-yl)-N-methyl-4-o-tolyl-nicotinamide, N-(3,5-bis-trifluoromethyl-benzyl)-6-(4-formyl-1-oxy-piperazin-1-yl)-N-methyl-4-o-tolyl-nicotinamide or 5'-[(3,5-bis-trifluoromethyl-benzyl)-methyl-carbamoyl]-4'-o-tolyl-1-oxy-3,4,5,6-tetrahydro-2H-[1,2']bipyridinyl-4-carboxylic acid.

Examples of compounds of formuls I, further comprising $R^2$, $R^{2'}$ being adjacent and taken together with the ring carbons to which they are attached to form —CH=CH—CH=CH—, are the followings:

N-methyl-N-(2-methyl-naphthalen-1-ylmethyl)-6-(4-oxy-morpholin-4-yl)-4-o-tolyl-nicotinamide, N-methyl-6-(4-oxy-morpholin-4-yl)-N-naphthalen-1-ylmethyl-4-o-tolyl-nicotinamide, N-(2-methoxy-naphthalen-1-ylmethyl)-N-methyl-6-(4-oxy-morpholin-4-yl)-4-o-tolyl-nicotinamide, N-methyl-6-(4-oxy-morpholin-4-yl)-N-naphthalen-2-ylmethyl-4-o-tolyl-nicotinamide or N-(1,4-dimethoxy-naphthalen-2-ylmethyl)-N-methyl-6-(4-oxy-morpholin-4-yl)-4-o-tolyl-nicotinamide.

The present compounds of formula I and their pharmaceutically acceptable salts can be prepared by methods known in the art, for example, by processes described below, which process comprises oxidizing a compound of formula

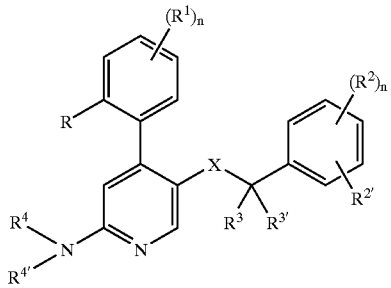

II with a suitable oxidizing agent to give a compound of formula

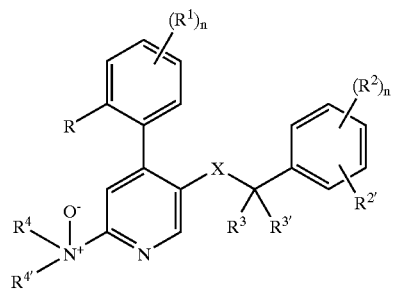

I wherein the substituents have the significances given above, and if desired, converting the compound obtained into a pharmaceutically acceptable acid addition salt.

In accordance with this procedure, a compound of formula I may be prepared, for example, as follows: To a solution of 10 mmol of a compound of formula II in 50 ml of a suitable solvent such as dichloromethane is added under ice cooling a solution of 10 mmol of a suitable oxidizing reagent such as 3-chloroperbenzoic acid in 50 ml of a suitable solvent such as dichloromethane. Stirring is continued for an appropriate time (typically 1 h to 24 h) at 0° C. and reaction progress may be followed by thin-layer-chromatography. In cases in which product formation is too slow, the reaction mixture may be stirred at room temperature. After evaporation of the solvent products of formula I can be isolated by flash-chromatography in 15% to 85% yield. Further purification of crystalline products may be achieved by recrystallization from a suitable solvent.

For this transformation other oxidizing reagents may be used instead of 3-chloroperbenzoic acid. Those oxidizing reagents are familiar to any person skilled in the art such as dimethyldioxirane in acetone, hydrogenperoxide in acetic acid or potassium peroxymonosulfate in a suitable solvent such as water.

The salt formation is effected at room temperature in accordance with methods which are known per se and which are familiar to any person skilled in the art. Not only salts with inorganic acids, but also salts with organic acids come into consideration. Hydrochlorides, hydrobromides, sulphates, nitrates, citrates, acetates, maleates, succinates, methan-sulphonates, p-toluenesulphonates and the like are examples of such salts.

The following schemes 1–8 describe the processes for preparation of compounds of formula I in more detail. The starting materials are known compounds and may be prepared according to methods known in the art, for example in accordance with methods, described in EP 1035115.

In the schemes the following abbreviations have been used:

| | |
|---|---|
| PivCl | pivaloyl chloride |
| THF | tetrahydrofuran |
| TMEDA | N,N,N',N'-tetramethylethylene diamine |
| DIPEA | N-ethyldiisopropyl-amine |
| KHMDS | potassium hexamethyldisilazide |

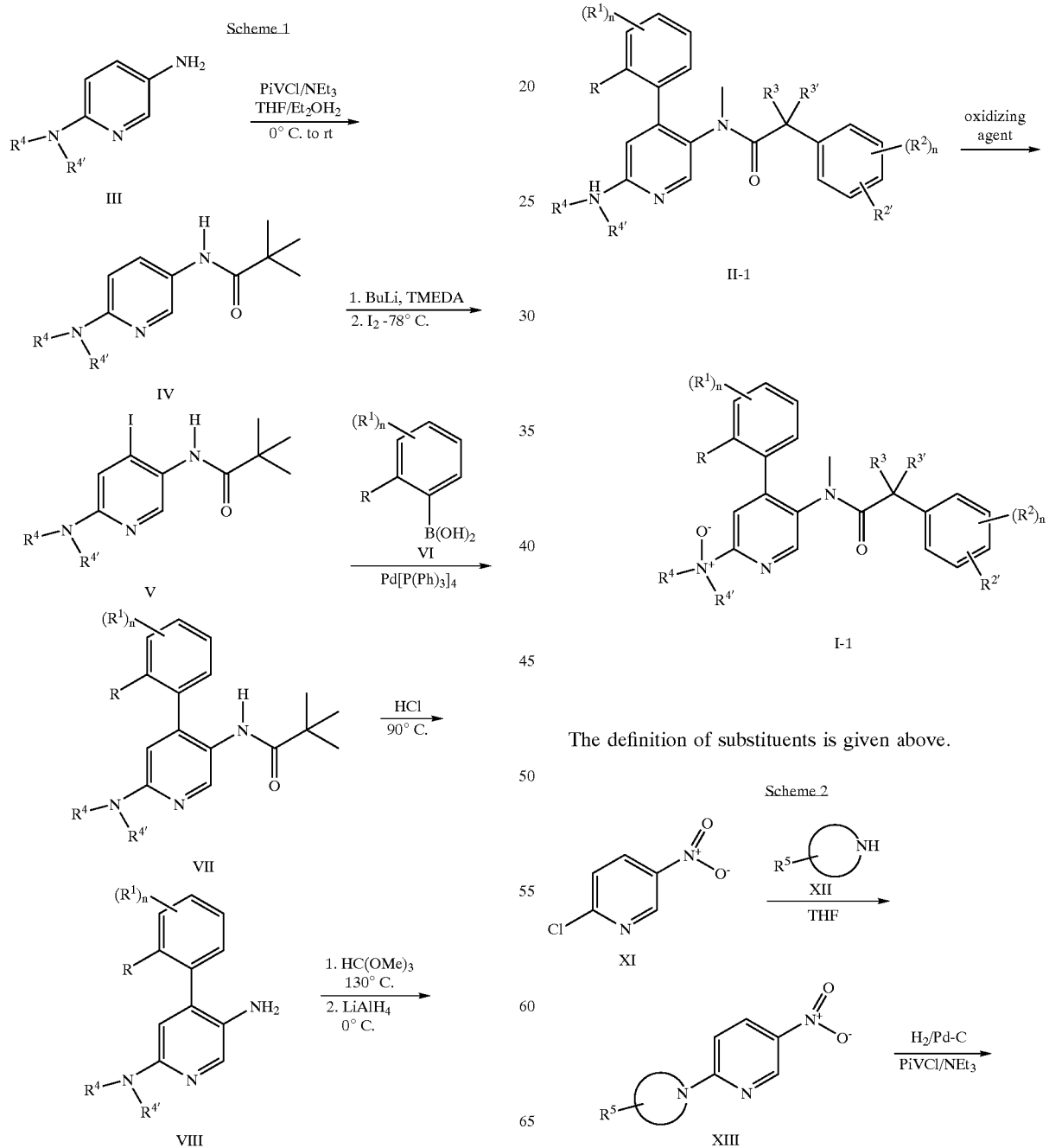

The definition of substituents is given above.

-continued
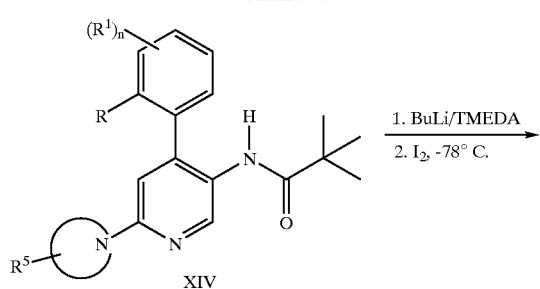
XIV
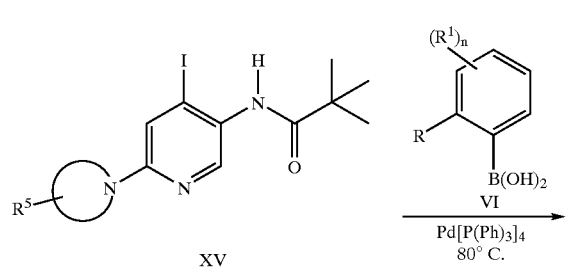
XV
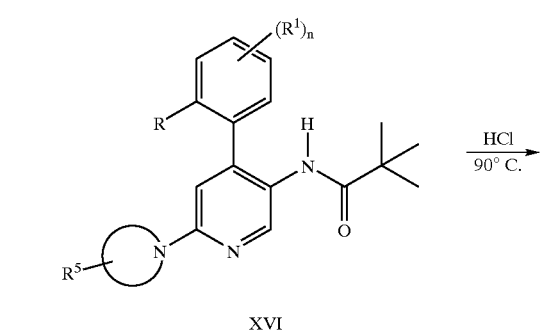
XVI
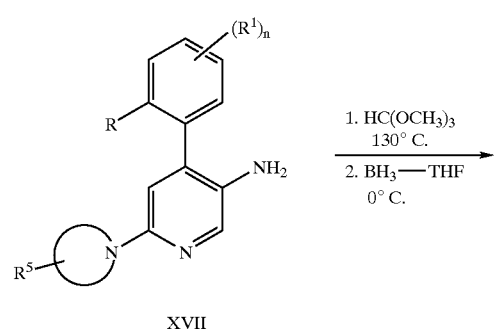
XVII
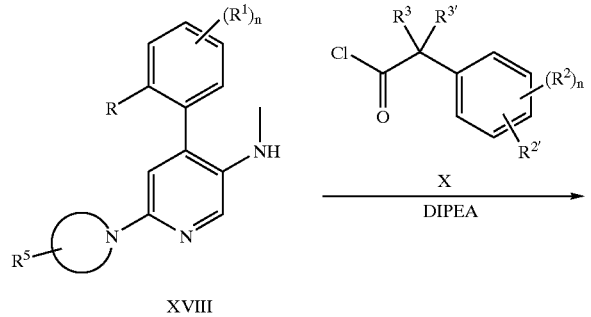
XVIII
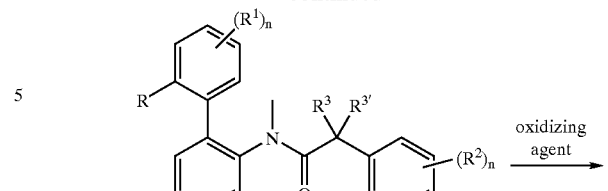
II-2
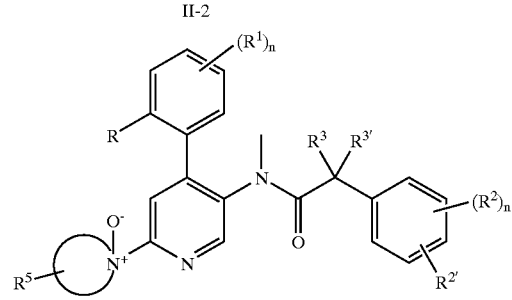
I-2
The definition of substituents is given above.
Scheme 3
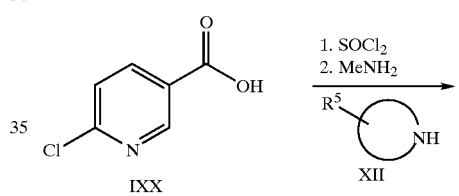
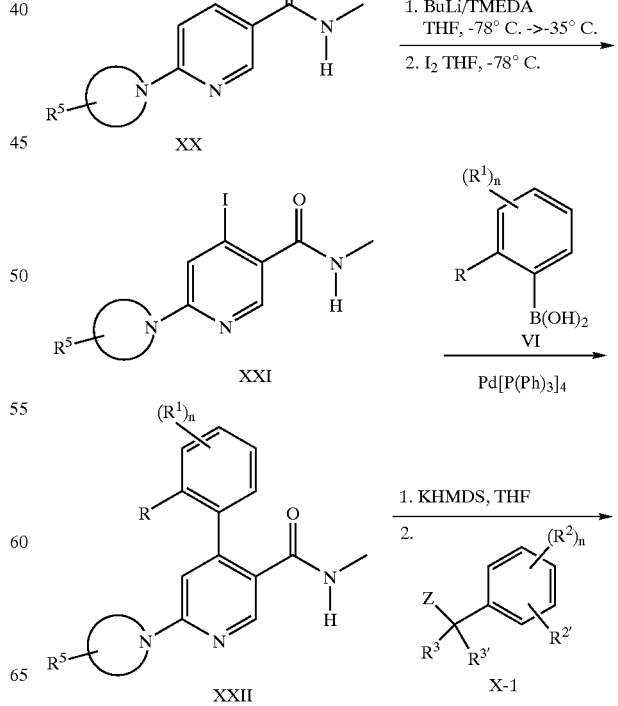

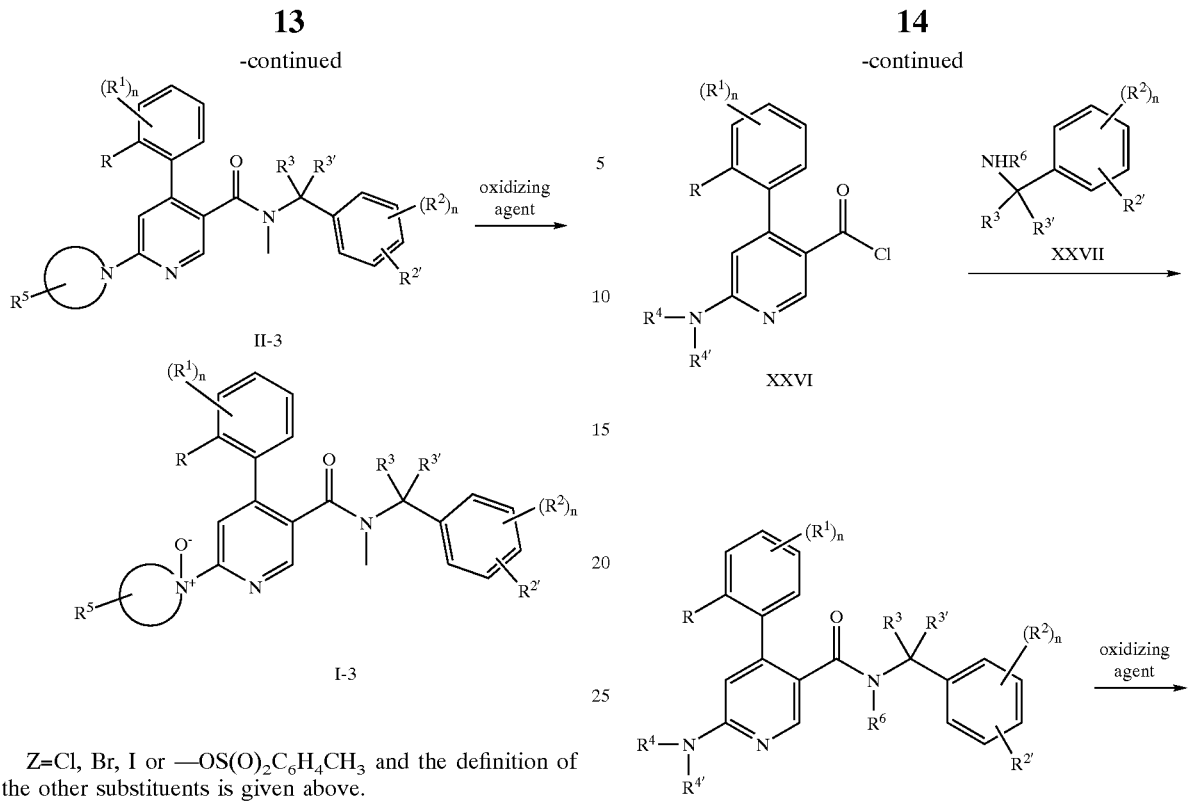
Z=Cl, Br, I or —OS(O)$_2$C$_6$H$_4$CH$_3$ and the definition of the other substituents is given above.
Scheme 4
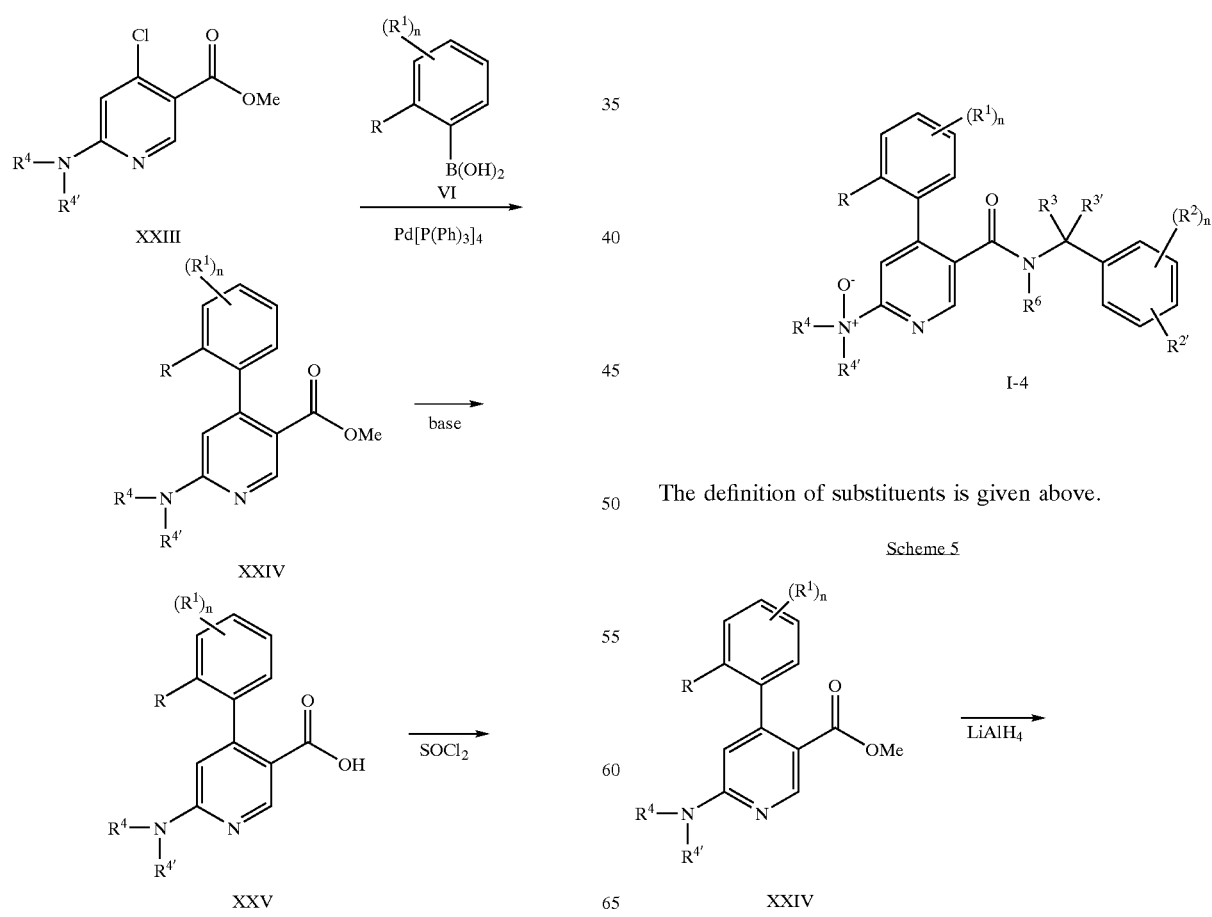
The definition of substituents is given above.
Scheme 5

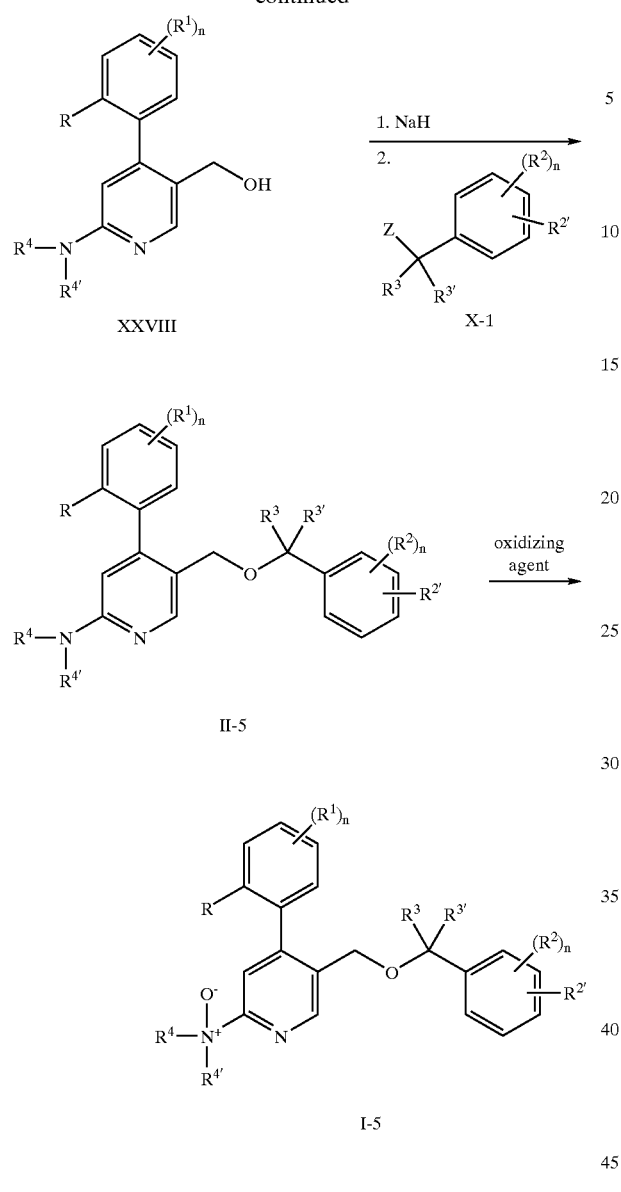
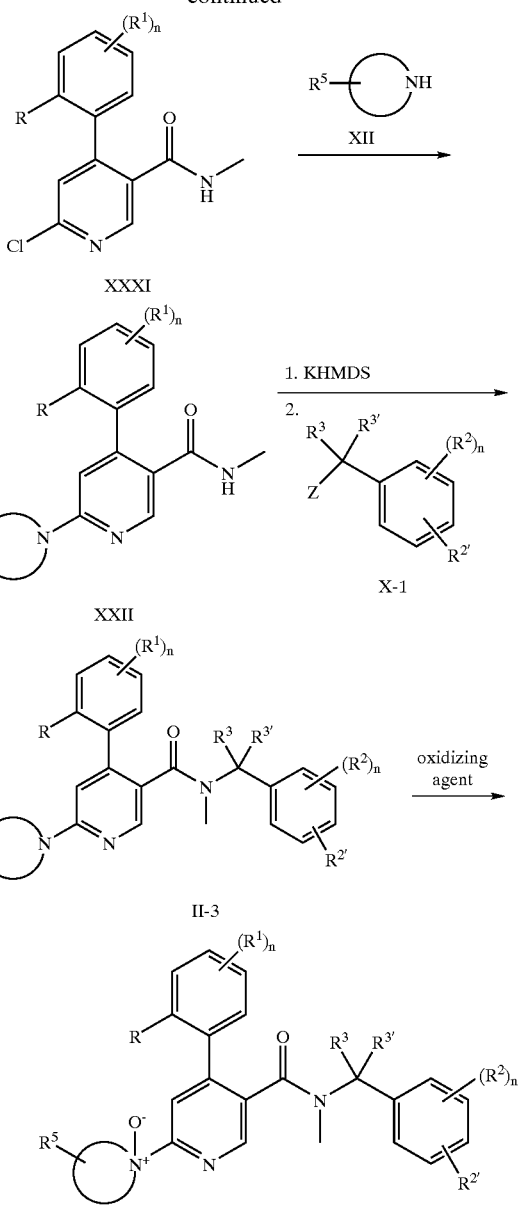
Z is Cl, Br, I or —OS(O)₂C₆H₄CH₃ and the definition of the other substituents is described above.
Scheme 6
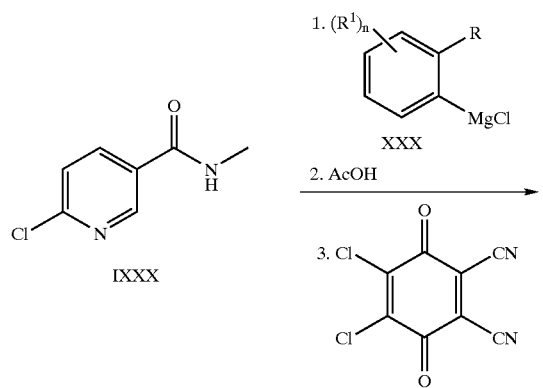
Z is Cl, Br, I or —OS(O)₂C₆H₄CH₃ and the definition of the other substituents is given above.
Scheme 7
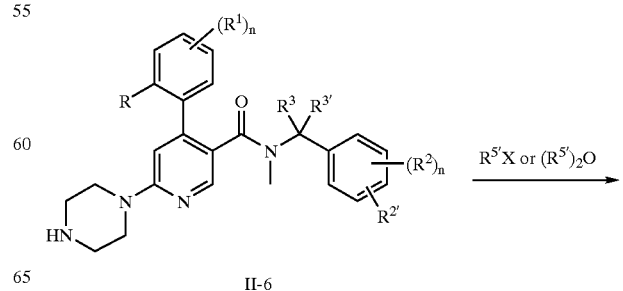

-continued

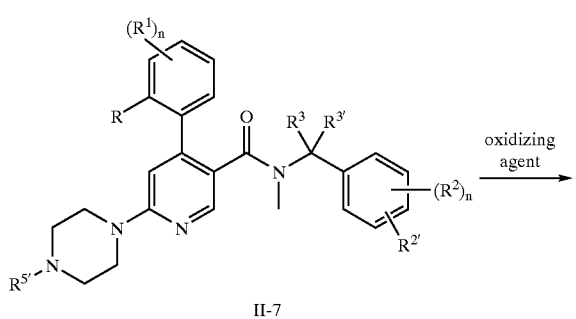

II-7

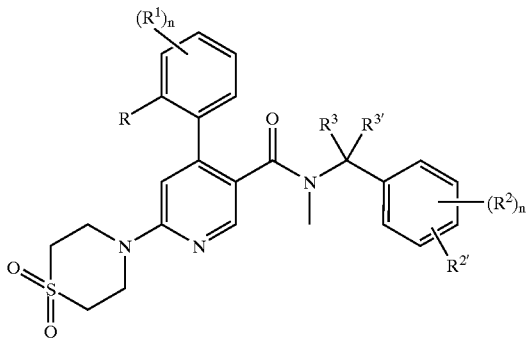

II-8

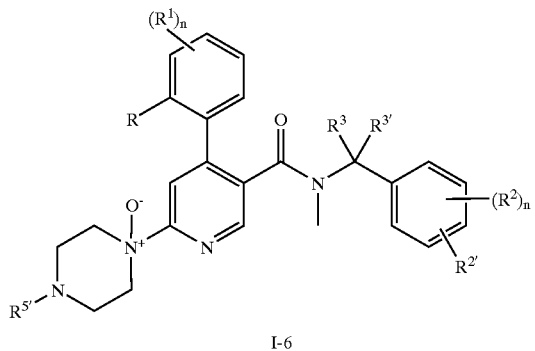

I-6

R⁵' is the group —C(O)R³ and the definition of the remaining substituents is given above.

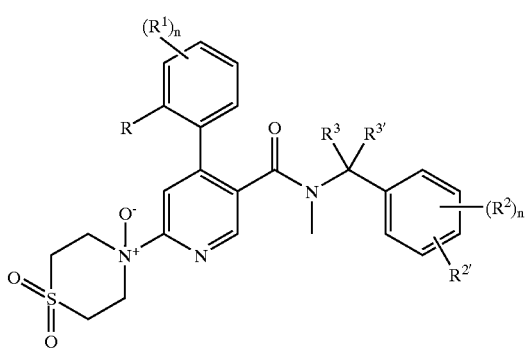

I-7

Scheme 8

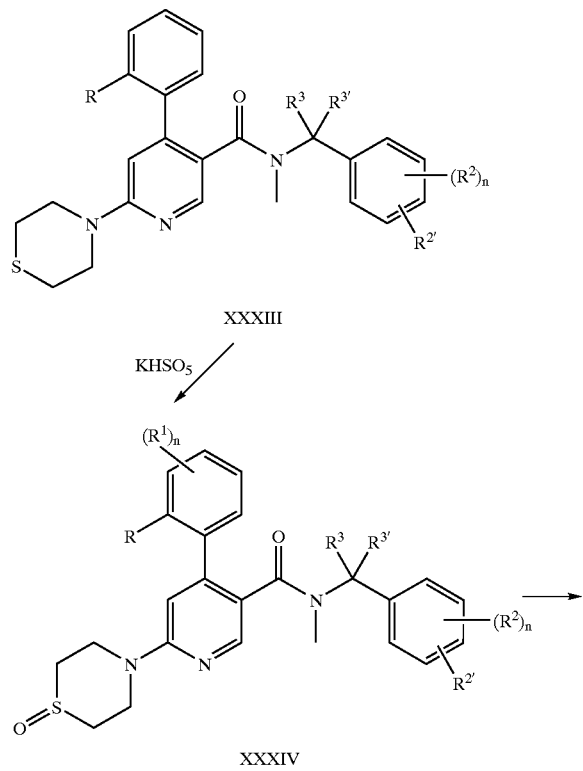

The definition of substituents is given above.

As mentioned earlier, the compounds of formula I and their pharmaceutically usable addition salts may be used as prodrugs of the parent compounds of formula II, which possess valuable pharmacological properties. These compounds are antagonists of the Neurokinin 1 (NK-1, substance P) receptor.

Furthermore, in addition, some N-oxides of formula I have a good affinity to the NK1 receptor. For some preferred compounds the pKi value is in the range of 8.3 to 8.7.

All of the preferred compounds of the invention were investigated in accordance with the tests given hereinafter.

Binding Assay (In Vitro)

The affinity of test compounds for the $NK_1$ receptor was evaluated at human $NK_1$ receptors in CHO cells infected with the human $NK_1$ receptor (using the Semliki virus expression system) and radiolabelled with [³H]substance P (final concentration 0.6 nM). Binding assays were performed in HEPES buffer (50 mM, pH 7.4) containing BSA (0.04%) leupeptin (8 μg/ml), $MnCl_2$ (3 mM) and phosphoramidon (2 μM). Binding assays consisted of 250 μl of membrane suspension (1.25×10⁵ cells/assay tube), 0.125 μl of buffer of displacing agent and 125 μl of [³H]substance P. Displacement curves were determined with at least seven concentrations of the compound. The assay tubes were incubated for 60 min at room temperature after which time the tube contents were rapidly filtered under vacuum through GF/C filters presoaked for 60 min with PEI (0.3%) with 2×2 ml washes of HEPES buffer (50 mM, pH 7.4). The radioactivity retained on the filters was measured by scintillation counting. All assays were performed in triplicate in at least 2 separate experiments.

The evidence, that the compounds of formula I may be used as prodrugs of their parent compounds of formula II is shown in accordance with the description given hereinafter.

The conversion of N-oxide prodrugs to the corresponding parent compounds is due to a reduction mechanism. There is some evidence from the literature that similar reactions occur in vivo and are probably catalysed by hemoglobin, hence the decision to study both the stability in plasma and blood was taken. The presence of an oxidant in the work-up solution should help preventing the reduction of the N-oxides.

Conversion in plasma: 10 µLs of a 100 µg/mL DMSO solution of the pro-drug were added to 1 mL plasma to reach a final concentration of 1 µg/mL. The incubation was performed at 37° C. and 8 aliquots were taken at different time points over 30 min. These aliquots were treated with 3 volumes of cold MeOH containing $H_2O_2$ (final concentration 10% v/v) and centrifuged at 3500 g for 20 min at 10° C. The supernatant was directly used to determine the drug levels by LC-MS-MS (HPLC chromatography on reversed phase column X-Terra MS C18 3.5 µM 2.1×30 mm Waters at 40° C., using a polarity gradient MeOH/Form.Ac.

1% 20/80/MeOH; run time; 3.0 min; inj. Vol.: 10 µL; Flow: 0.2 µL/min and MS/MS detection on a PE Sciex API-2000 MS/MS spectrometer; ion source: Turbospray; ionisation mode: ESP+).

Conversion in fresh blood: The same procedure was used for the stability studies in blood, even if much more care had to be taken after treatment with the $H_2O_2$.

Sample stability (plasma and blood): The final matrix were first prepared (plasma or blood treated with 3 volumes of cold MeOH containing $H_2O_2$—10% v/v—and centrifuged at 3500 g for 20 min at 10° C.) and then incubated at 37° C. into two tubes; the pro-drug or the drug were then incubated and finally their concentration determined by LC-MS-MS as described above.

The method used to stop the reaction in both plasma and blood was found to be enough reliable to perform the studies at least when the analysis was performed immediately after the incubations.

The half-life obtained for the conversion prodrug to drug in plasma are reported in the following table (Plasma sample preparation was found to be critical for exact determination of values for $t_{1/2}$):

| Example No. | t½ (hours) | | |
|---|---|---|---|
| | Dog plasma | Human plasma | Rat plasma |
| 1 | 18 | 8 | 4 |
| 2 | 18 | 12 | 5 |
| 16 | 16 | 6 | 2 |

The stability in blood is much lower ($t_{1/2}$<30 min) and it was impossible to determine a precise value of $t_{1/2}$. However we can conclude that there are no major species difference with respect with stability in blood and that the prodrugs are converted to the desired drugs in high yield. (>90%).

In accordance with the tests the compounds of formula I can function as prodrugs of their parent compounds of formula II.

The compounds of formula I as well as their pharmaceutically usable acid addition salts can be used as medicaments, e.g. in the form of pharmaceutical preparations. The pharmaceutical preparations can be administered orally, e.g. in the form of tablets, coated tablets, dragées, hard and soft gelatine capsules, solutions, emulsions or suspensions. The administration can, however, also be effected rectally, e.g. in the form of suppositories, or parenterally, e.g. in the form of injection solutions.

The compounds of formula I and their pharmaceutically usable acid addition salts can be processed with pharmaceutically inert, inorganic or organic excipients for the production of tablets, coated tablets, dragees and hard gelatine capsules. Lactose, corn starch or derivatives thereof, talc, stearic acid or its salts etc can be used as such excipients e.g. for tablets, dragées and hard gelatine capsules.

Suitable excipients for soft gelatine capsules are e.g. vegetable oils, waxes, fats, semi-solid and liquid polyols etc.

Suitable excipients for the manufacture of solutions and syrups are e.g. water, polyols, saccharose, invert sugar, glucose etc.

Suitable excipients for injection solutions are e.g. water, alcohols, polyols, glycerol, vegetable oils etc.

Suitable excipients for suppositories are e.g. natural or hardened oils, waxes, fats, semi-liquid or liquid polyols etc.

Moreover, the pharmaceutical preparations can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The dosage can vary within wide limits and will, of course, be fitted to the individual requirements in each particular case. In general, in the case of oral administration a daily dosage of about 10 to 1000 mg per person of a compound of formula I should be appropriate, although the above upper limit can also be exceeded when necessary.

The following preferred examples illustrate the present invention without limiting it. All temperatures are given in degrees Celsius.

The preparation of compounds of formula I, starting with compounds of formula II, is described generically in the description. This oxidation procedure is always the last step to obtain the N-oxides of compounds of formula I. A detailed description of this last step is specifically described in the following examples 1, 2 and 13. The N-oxidation of the remaining compounds 3 to 12 and 14 to 29 is generically described in accordance with the above mentioned description.

EXAMPLE 1

2-(3,5-Bis-trifluoromethyl-phenyl)-N-methyl-N-[6-(4-oxy-morpholin-4-yl)-4-o-tolyl-pyridin-3-yl]-isobutyramide a) 4-(5-Nitro-2-pyridyl)-morpholine To a solution of 20 g (126 mmol) of 2-chloro-5-nitropyridine in 150 ml tetrahydrofuran were added dropwise 27 ml (315 mmol) morpholine within 10 min. The reaction mixture was refluxed for additional 2 h. After cooling to room temperature, the solvent was removed in vacuo and the residue was re-dissolved in 200 ml ethyl acetate. The organic phase was washed with 200 ml 1 N sodium bicarbonate solution, dried (magnesium sulfate) and evaporated to give 27.3 g (quantitative) of the title compound as a yellow solid. M.p. 142–143° C.

b) 2,2-Dimethyl-N-(6-morpholin-4-yl-pyridin-3-yl)-propionamide

To a solution of 27.3 g (126 mmol) of 4-(5-nitro-2-pyridyl)-morpholine in 600 ml methanol were added 2.5 g of 10% of palladium on activated charcoal. The reaction mixture was hydrogenated (room temperature to ca. 45° C., 1 bar) until the theoretical amount of hydrogen was taken up (about 3 h). The catalyst was filtered off and was washed twice with 100 ml portions of methanol. The filtrate was evaporated in vacuo to give 22.6 g of a purple oil which consisted to ca 95% of the desired aniline derivative according to analysis by thin layer chromatography.

This crude product was dissolved in a mixture of 240 ml tetrahydrofuran and 60 ml diethyl ether. After cooling to 0° C., 26 ml (189 mmol) of triethylamine were added in one portion. Stirring was continued while 23 g (189 mmol) of pivaloyl chloride were added dropwise within a period of 10 min. The ice bath was removed and the reaction mixture was stirred for 1 h at room temperature. Then, the solvent was removed in vacuo and the residue was suspended in 200 ml 1 N sodium bicarbonate solution. The product was extracted three times with 200 ml portions of dichloromethane, dried (sodium sulfate) and evaporated. Recrystallization of the solid residue from ethyl acetate/hexane 1:8 gave 28.6 g (86%) of the title compound as white crystals.

MS m/e (%): 264 (M+H$^+$, 100).

c) N-(4-Iodo-6-morpholin-4-yl-pyridin-3-yl)-2,2-dimethyl-propionamide

A solution of 28.4 g (108 mmol) 2,2-dimethyl-N-(6-morpholin-4-yl-pyridin-3-yl)-propionamide and 49 ml (324 mmol) N,N,N',N'-tetramethylethylenediamine under argon in 600 ml tetrahydrofuran was cooled in a dry ice bath to −78° C. Within 1 h, 202 ml (324 mmol) of a 1.6 N n-butyllithium solution in hexane were added dropwise. The reaction mixture was allowed to warm up to −35° C. overnight. After cooling again to −78° C., 37 g (146 mmol) iodine dissolved in 60 ml tetrahydrofuran were added dropwise during 15 min. The dry ice bath was replaced by an ice bath and a solution of 90 g (363 mmol) sodium thiosulfate pentahydrate in 250 ml water were added within 10 min when the temperature of the reaction mixture had reached 0° C. Then, 1000 ml diethyl ether were added and the organic layer was separated. The aqueous layer was extracted twice with 500 ml dichloromethane and the combined organic layers were dried (magnesium sulfate) and evaporated. Flash chromatography gave 15.6 g (37%) of the title compound as a light brown oil which crystallized upon standing at room temperature.

MS m/e (%): 389 (M$^+$, 71), 358 (25), 304 (43), 57 (100).

d) 2,2-Dimethyl-N-(6-morpholin-4-yl-4-o-tolyl-pyridin-3-yl)-propionamide

A mixture of 3.50 g (9.0 mmol) N-(4-iodo-6-morpholin-4-yl-pyridin-3-yl)-2,2-dimethyl-propionamide, 35 ml toluene, 18 ml 2 N sodium carbonate solution, 312 mg (0.27 mmol) tetrakis(triphenylphosphine)palladium(0) and 1.34 g (9.9 mmol) o-tolylboronic acid was heated under argon at 80° C. for 12 h. After cooling to room temperature, the aqueous phase was separated and washed twice with ethyl acetate. The combined organic layers were washed with 50 ml brine, dried (sodium sulfate) and evaporated. Purification by flash-chromatography gave 3.23 g (quantitative) of the title compound as a white foam.

MS m/e (%): 354 (M+H$^+$, 100).

e) 6-Morpholin-4-yl-4-o-tolyl-pyridin-3-ylamine

A suspension of 2.93 g (8.28 mmol) 2,2-dimethyl-N-(6-morpholin-4-yl-4-o-tolyl-pyridin-3-yl)-propionamide in 80 ml 3 N hydrochloric acid solution and 5 ml 1-propanol was heated to 90–95° C. overnight. The reaction mixture was cooled to room temperature, washed with three 20 ml portions diethyl ether and filtered over celite. The filtrate was diluted with 20 ml water and was adjusted to pH 7–8 by addition of 28% sodium hydroxide solution under ice cooling. The product was extracted with four 100 ml portions of dichloromethane. The combined organic layers were washed with 50 ml brine, dried (magnesium sulfate) and evaporated to give 2.31 g (quantitative) of the title compound as a white foam.

MS m/e (%): 269 (M$^+$, 100).

f) Methyl-(6-morpholin-4-yl-4-o-tolyl-pyridin-3-yl)-amine

A solution of 2.24 g (8.3 mmol) 6-morpholin-4-yl-4-o-tolyl-pyridin-3-ylamine in 17 ml trimethyl orthoformate and 3 drops trifluoroacetic acid was heated for 2 h at 130° C. The reaction mixture was evaporated and dried in vacuo for 30 min. The residual oil was dissolved in 5 ml tetrahydrofuran and was added dropwise under ice cooling to 630 mg (16.6 mmol) lithium aluminum hydride in 20 ml tetrahydrofuran. The reaction mixture was stirred for 1 h at room temperature, cooled to 0° C. again and acidified (pH 1–2) by addition of 28% hydrochloric acid solution. After stirring for 5 min, 28% sodium hydroxide solution was added to reach pH 10. The solution was filtered over celite, evaporated and purified by flash chromatography to give 1.56 g (66%) of the title compound as a white foam.

MS m/e (%): 283 (M$^+$, 100).

g) 2-(3,5-Bis-trifluoromethyl-phenyl)-N-methyl-N-(6-morpholin-4-yl-4-o-tolyl-pyridin-3-yl)-isobutyramide A solution of 1.46 g (5.15 mmol) methyl-(6-morpholin-4-yl-4-o-tolyl-pyridin-3-yl)-amine and 1.32 ml (7.73 mmol) N-ethyldiisopropylamine in 15 ml dichloromethane was cooled in an ice bath and 1.8 g (5.67 mmol) 2-(3,5-bis-trifluoromethyl-phenyl)-2-methyl-propionyl chloride were added dropwise. The reaction mixture was warmed to 35–40° C. for 3 h, cooled to room temperature again and was stirred with 25 ml saturated sodium bicarbonate solution. The organic layer was separated and the aqueous phase was extracted with dichloromethane. The combined organic layers were dried (magnesium sulfate) and evaporated. The residue was purified by flash chromatography to give 2.9 g (quantitative) of the title compound as white crystals.

M.p. 131–132° C.

h) 2-(3,5-Bis-trifluoromethyl-phenyl)-N-methyl-N-[6-(4-oxy-morpholin-4-yl)-4-o-tolyl-pyridin-3-yl]-isobutyramide To a solution of 5.0 g (8.84 mmol) 2-(3,5-bis-trifluoromethyl-phenyl)-N-methyl-N-(6-morpholin-4-yl-4-o-tolyl-pyridin-3-yl)-isobutyramide in 50 ml dichloromethane was added under ice cooling a soloution of 2.18 g (8.84 mmol) of 3-chloroperbenzoic acid (ca. 70%) in 35 ml dichloromethane. After stirring for 1 h at 0° C., 2.6 g (25.7 mmol) triethylamine were added slowly. The reaction mixture was concentrated to a total volume of 10 mL and the residue was purified by flash-chromatography. The crude material was suspended in 20 ml diethyl ether, filtered and dried in vacuo to give 4.2 g (82%) of the title compound as white crystals. M.p. 149–151° C. (partial decomposition).

MS m/e (%): 582 (M+H$^+$, 100).

EXAMPLE 2

2-(3,5-Bis-trifluoromethyl-phenyl)-N-[4-(2-chloro-phenyl)-6-(4-oxy-morpholin-4-yl)-pyridin-3-yl]-N-methyl-isobutyramide The title compound was obtained as white crystals in comparable yields according to the procedures described above for Example 1 using 2-chlorophenylboronic acid instead of o-tolylboronic acid in step d). M.p.141–143° C. (partial decomposition), MS m/e (%): 602 (M+H$^+$, 100), 624 (M+Na$^+$, 10).

EXAMPLE 3

2-(3,5-Bis-trifluoromethyl-phenyl)-N-[6-(4-oxy-morpholin-4-yl)-4-o-tolyl-pyridin-3-yl]-isobutyramide The parent compound was obtained as white powder in comparable yields according to the procedures described above for the preparation of Example 1 in steps a) to g). Step f) was omitted.

MS m/e (%): 552 (M+H⁺, 100).

The N-oxide was obtained in accordance with step h) in Example 1.

EXAMPLE 4

2-(3,5-Bis-trifluoromethyl-phenyl)-N-[4'-(2-chloro-phenyl)-1-oxy-3,4,5,6-tetrahydro-2H-[1,2']bipyridinyl-5'-yl]-N-methyl-isobutyramide The parent compound was obtained as a white powder in comparable yields according to the procedures described above for the preparation of Example 1 in steps a) to g) using piperidine instead of morpholine in step a) and using 2-chlorophenylboronic acid instead of o-tolylboronic acid in step d).

MS m/e (%): 583 (M⁺, 20), 296 (78), 255 (100).

The N-oxide was obtained in accordance with step h) in Example 1.

EXAMPLE 5

2-(3,5-Bis-trifluoromethyl-phenyl)-N-(6-oxy-dimethylamino-4-o-tolyl-pyridin-3-yl)-N-methyl-isobutyramide The parent compound was obtained as white solid in comparable yields according to the procedures described above for the preparation of Example 1, steps a) to g) using dimethylamine hydrochloride instead of morpholine in step a). M.p. 174–175° C., MS m/e (%): 524 (M+H⁺, 100).

The N-oxide was obtained in accordance with step h) in Example 1.

EXAMPLE 6

2-(3,5-Bis-trifluoromethyl-phenyl)-N-[4-(2-chloro-phenyl)-6-oxy-dimethylamino-pyridin-3-yl]-isobutyramide The parent compound was obtained as white solid in comparable yields according to the procedures described above for the preparation of Example 1 steps a) to g) using dimethylamine hydrochloride instead of morpholine in step a) and using 2-chlorophenylboronic acid instead of o-tolylboronic acid in step d). M.p. 162–163° C.

MS m/e (%): 544 (M+H⁺, 100).

The N-oxide was obtained in accordance with step h) in Example 1.

EXAMPLE 7

2-(3,5-Bis-trifluoromethyl-phenyl)-N-1-(4-hydroxy-1-oxy-4'-o-tolyl-3,4,5,6-tetrahydro-2H-[1,2']bipyridinyl-5'-yl)-N-methyl-isobutyramide The parent compound was obtained as white foam in comparable yields according to the procedures described above for the preparation of Example 1 steps a) to g) using 4-hydroxypiperidine instead of morpholine in step a).

MS m/e (%): 580 (M+H⁺, 100).

The N-oxide was obtained in accordance with step h) in Example 1.

EXAMPLE 8

2-(3,5-Bis-trifluoromethyl-phenyl)-N-{6-[(2-hydroxy-ethyl)-1-oxy-methyl-amino]-4-o-tolyl-pyridin-3-yl}-N-methyl-isobutyramide The parent compound was obtained as white foam in comparable yields according to the procedures described above for the preparation of Example 1 in steps a) to g) using N-methylethanolamine instead of morpholine in step a).

MS m/e (%): 554 (M+H⁺, 100).

The N-oxide was obtained in accordance with step h) in Example 1.

EXAMPLE 9

(R)-2-(3,5-Bis-trifluoromethyl-phenyl)-N-[6-(3-hydroxy-1-oxy-pyrrolidin-1-yl)-4-o-tolyl-pyridin-3-yl]-N-methyl-isobutyramide The parent compound was obtained as white foam in comparable yields according to the procedures described above for the preparation of Example 1 in steps a) to g) using (R)-3-hydroxypyrrolidine instead of morpholine in step a).

MS m/e (%): 566 (M+H⁺, 100).

The N-oxide was obtained in accordance with step h) in Example 1.

EXAMPLE 10

2-(3,5-Bis-trifluoromethyl-phenyl)-N-methyl-N-[6-(4-oxy-morpholin-4-yl)-4-o-tolyl-pyridin-3-yl]-acetamide To a solution of 300 mg (1.1 mmol) 3,5-bis(trifluoromethyl)-phenylacetic acid in 7 ml N,N-dimethylformamide were added 185 mg (1.14 mmol) 1,1'-carbonyl-diimidazole and the solution was stirred for 30 min at room temperature. After addition of 283 mg (1 mmol) of methyl-(6-morpholin-4-yl-4-tolyl-pyridin-3-yl)-amine (as described in step f) for the preparation of Example 1), the reaction mixture was heated over night at 90° C. After cooling to room temperature, the solvent was removed in vacuo and the residue was re-dissolved in 30 ml ethyl acetate. The organic phase was washed with water (2×30 ml), brine, dried (magnesium sulfate) and evaporated. Flash chromatography gave 506 mg (94%) of the parent compound as a light brown foam.

MS m/e (%): 538 (M+H⁺, 100).

The N-oxide was obtained in accordance with step h) in Example 1.

EXAMPLE 11

2-(3,5-Dimethoxy-phenyl)-N-methyl-N-[6-(4-oxy-morpholin-4-yl)-4-o-tolyl-pyridin-3-yl]-acetamide To a solution of 226 mg (1.15 mmol) 3,5-dimethoxy-phenylacetic acid in 7 ml N,N-dimethylformamide were added 244 mg (1.5 mmol) 1,1'-carbonyl-diimidazole and the solution was stirred for 30 min at room temperature. After addition of 283 mg (1 mmol) of methyl-(6-morpholin-4-yl-4-tolyl-pyridin-3-yl)-amine (as described in step f) for the preparation of Example 1), the reaction mixture was heated at 70° C. for 7 h. After cooling to room temperature, the solvent was removed in vacuo and the residue was re-dissolved in 30 ml ethyl acetate. The organic phase was washed with water (2×30 ml), brine, dried (magnesium sulfate) and evaporated. Flash chromatography gave 347 mg (75%) of the parent compound as a white foam.

MS m/e (%): 462 (M+H⁺, 100).

The N-oxide was obtained in accordance with step h) in Example 1.

EXAMPLE 12

2-(3-Fluoro-5-trifluoromethyl-phenyl)-N-methyl-N-[6-(4-oxy-morpholin-4-yl)-4-o-tolyl-pyridin-3-yl]-acetamide To a solution of 266 mg (1.2 mmol) 3-fluoro-5-trifluoromethyl-phenylacetic acid in 7 ml N,N- dimethylformamide were added 195 mg (1.2 mmol) 1,1'-carbonyl-diimidazole and the solution was stirred for 30 min at room temperature. After addition of 283 mg (1 mmol) of methyl-(6-morpholin-4-yl-4-tolyl-pyridin-3-yl)-amine (as described in step f) for the preparation of Example 1), the reaction mixture was heated at 90° C. for 6 h. After cooling to room temperature, the solvent was removed in vacuo and the residue was re-dissolved in 30 ml ethyl acetate. The organic phase was washed with water (2×30 ml), brine, dried (magnesium sulfate) and evaporated. Flash chromatography gave 432 mg (88%) of the parent compound as a light yellow foam.

MS m/e (%): 488 (M+H$^+$, 100).

The N-oxide was obtained in accordance with step h) in Example 1.

EXAMPLE 13

4-{5-[(3,5-Bis-trifluoromethyl-benzyl)-methyl-carbamoyl]-4-o-tolyl-pyridin-2-yl}-4-oxy-piperazine-1-carboxylic acid tert-butyl ester a) 6-Chloro-N-methyl-4-o-tolyl-nicotinamide To a solution of 3.41 g (20.0 mmol) 6-chloro-N-methyl-nicotinamide in 80 ml tetrahydrofuran 50 ml (50 mmol) of a 1 M solution of o-tolyl magnesium chloride in tetrahydrofuran was added dropwise at 0° C. After completed addition the reaction mixture was allowed to warm to room temperature and stirred for 1.5 h. The mixture was again cooled to 0° C., followed by the dropwise addition of 5.7 ml (100 mmol) acetic acid and a solution of 5.1 g (22 mmol) 2,3-dichloro-5,6-dicyano-1,4-benzoquinone in 18 ml tetrahydrofuran. After completed addition the reaction mixture was allowed to warm to room temperature and stirred for 15 min. Addition of 30 ml 2 N aqueous sodium hydroxide solution was followed by dilution with 1 l ethyl acetate and 200 ml water. The layers were separated and the organic layer was washed with 4 250-ml portions of 2 N aqueous sodium hydroxide solution. The combined aqueous layers were extracted with 3 500-ml portions of ethyl acetate. The combined organic extracts were washed with saturated aqueous sodium chloride solution and dried with sodium sulfate. Concentration gave 5.44 g of a brown-red oil. Flash column chromatography afforded 2.15 g (41.3%) of the title compound as a light yellow solid.

MS m/e (%): 260 (M+, 11), M.p. 91–93° C.

b) 4-(5-Methylcarbamoyl-4-o-tolyl-pyridin-2-yl)-piperazine-1-carboxylic acid tert-butyl ester A mixture of 8.31 g (31.9 mmol) 6-chloro-N-methyl-4-o-tolyl-nicotinamide, 6.53 g (35.0 mmol) 1-tert-butoxycarbonyl piperazine, 16.7 ml (95.6 mmol) N-ethyldiisopropylamine and a catalytic amount of 4-(N,N-dimethylamino)-pyridine was heated at reflux over night. After cooling to room temperature the mixture was dissolved in dichloromethane and washed with two portions of 0.1 N aqueous hydrochloric acid solution. Drying with sodium sulfate and concentration gave 10.7 g of the crude product. Flash column chromatography afforded 6.28 g (48.0%) of the title compound as an off-white solid.

MS m/e (%): 411 (M+H$^+$, 100).

c) 4-{5-[(3,5-Bis-trifluoromethyl-benzyl)-methyl-carbamoyl]-4-o-tolyl-pyridin-2-yl}-piperazine-1-carboxylic Acid Tert-Butyl Ester To a solution of 6.28 g (15.3 mmol) 4-(5-methylcarbamoyl-4-o-tolyl-pyridin-2-yl)-piperazine-1-carboxylic acid tert-butyl ester in 250 ml tetrahydrofuran 20 ml of a 1 M solution (20 mmol) of potassium hexamethyl-disilazide in tetrahydrofuran were added at 0° C. After 30 min, 2.81 ml (15.3 mmol) 3,5-bis(trifluoromethyl)benzyl bromide were added dropwise. The reaction mixture was allowed to warm to room temperature over night. Addition of water and 1 M aqueous sodium hydroxide solution was followed by extraction with three portions of ethyl acetate. The combined organic extracts were dried with sodium sulfate and concentrated. Flash column chromatography gave 6.89 g (70.8%) of the parent compound as a white solid.

MS m/e (%): 637 (M+H$^+$, 100).

The N-oxide was obtained in accordance with step h) in Example 1.

EXAMPLE 14

5'-[(3,5-Bis-trifluoromethyl-benzyl)-methyl-carbamoyl]-4'-o-tolyl-1-oxy-3,4,5,6-tetrahydro-2H-[1,2']bipyridinyl-4-carboxylic acid ethyl ester The parent compound was obtained as a white solid in comparable yields according to the procedures described above for the preparation of 4-{5-[(3,5-bis-trifluoromethyl-benzyl)-methyl-carbamoyl]-4-o-tolyl-pyridin-2-yl}-piperazine-1-carboxylic acid tert-butyl ester (Example 13) using ethyl isonipecotate instead of 1-tert-butoxycarbonyl piperazine in step b) and using 5'-methylcarbamoyl-4'-o-tolyl-3,4,5,6-tetrahydro-2H-[1,2']bipyridinyl-4-carboxylic acid ethyl ester instead of 4-(5-methylcarbamoyl-4-o-tolyl-pyridin-2-yl)-piperazine-1-carboxylic acid tert-butyl ester in step c).

MS m/e (%): 608 (M+H$^+$, 100).

The N-oxide was obtained in accordance with step h) in Example 1.

EXAMPLE 15

(RS)-6-[3-(Acetyl-methyl-amino)-1-oxo-pyrrolidin-1-yl]-N-(3,5-bis-trifluoromethyl-benzyl)-N-methyl-4-o-tolyl-nicotinamide The parent compound was obtained as a light-yellow solid in comparable yields according to the procedures described above for the preparation of 4-{5-[(3,5-bis-trifluoromethyl-benzyl)-methyl-carbamoyl]-4-o-tolyl-pyridin-2-yl}-piperazine-1-carboxylic acid tert-butyl ester (Example 13) using (RS)-3-(acetyl-methyl-amino)-pyrrolidine instead of 1-tert-butoxycarbonyl piperazine in step b) and using (RS)-6-[3-(acetyl-methyl-amino)-pyrrolidin-1-yl]-N-methyl-4-o-tolyl-nicotinamide instead of 4-(5-methylcarbamoyl-4-o-tolyl-pyridin-2-yl)-piperazine-1-carboxylic acid tert-butyl ester in step c).

MS m/e (%): 593 (M+H$^+$, 100).

The N-oxide was obtained in accordance with step h) in Example 1.

EXAMPLE 16

N-(3,5-Bis-trifluoromethyl-benzyl)-N-methyl-6-(4-oxy-morpholin-4-yl)-4-o-tolyl-nicotinamide monohydrate a) 6-Chloro-N-methyl-nicotinamide To 50 g (317 mmol) of 2-chloronicotinic acid were added 230 ml (3.16 mol) thionyl chloride at 0° C. After heating the mixture at reflux for 2 h excess thionyl chloride was removed by distillation. The oily brown residue was dissolved in 250 ml dichloromethane. The solution was treated with methylamine gas at 0° C. until no exothermic reaction was observed any longer. The resulting suspension was diluted with 1000 ml dichloromethane/water. The layers were separated and the aqueous layer extracted with three 300-ml portions of dichloromethane. Drying of the combined organic layers with sodium sulfate and concentration gave 53.2 g (98%) of the title compound as a light yellow solid.

MS m/e (%): 171 (M+H$^+$, 15).

b) 6-Chloro-N-methyl-4-o-tolyl-nicotinamide

To a solution of 3.41 g (20.0 mmol) 6-chloro-N-methyl-nicotinamide in 80 ml tetrahydrofuran 50 ml (50 mmol) of a 1 M solution of o-tolyl magnesium chloride in tetrahydrofuran was added dropwise at 0° C. After completed addition the reaction mixture was allowed to warm to room temperature and stirred for 1.5 h. The mixture was again cooled to 0° C., followed by the dropwise addition of 5.7 ml (100 mmol) acetic acid and a solution of 5.1 g (22 mmol) 2,3-dichloro-5,6-dicyano-1,4-benzoquinone in 18 ml tetrahydrofuran. After completed addition the reaction mixture was allowed to warm to room temperature and stirred for 15 min. Addition of 30 ml 2 N aqueous sodium hydroxide solution was followed by dilution with 1 l ethyl acetate and 200 ml water. The layers were separated and the organic layer was washed with 4 250-ml portions of 2 N aqueous sodium hydroxide solution. The combined aqueous layers were extracted with 3 500-ml portions of ethyl acetate. The combined organic extracts were washed with saturated aqueous sodium chloride solution and dried with sodium sulfate. Concentration gave 5.44 g of a brown-red oil. Flash column chromatography afforded 2.15 g (41.3%) of the title compound as a light yellow solid.

M.p. 91–93° C. MS m/e (%): 260 (M$^+$, 11).

c) N-Methyl-6-morpholin-4-yl-4-o-tolyl-nicotinamide

A mixture of 1.00 g (3.84 mmol) 6-chloro-N-methyl-4-o-tolyl-nicotinamide, 0.37 ml (4.22 mmol) morpholine, 2.0 ml (12 mmol) N-ethyldiisopropylamine and a catalytic amount of 4-(N,N-dimethylamino)-pyridine was heated at 100° C. over night. After cooling to room temperature the mixture was dissolved in ethyl acetate and washed with two portions of water. The combined aqueous layers were extracted with 3 portions of dichloromethane. Drying with sodium sulfate and concentration gave 1.23 g of the crude product. Flash column chromatography afforded 1.11 g (92.9%) of the title compound as an off-white solid. M.p. 156–158° C.

MS m/e (%): 311 (M$^+$, 64).

d) N-(3,5-Bis-trifluoromethyl-benzyl)-N-methyl-6-morpholin-4-yl-4-o-tolyl-nicotinamide To a solution of 0.27 g (0.87 mmol) N-methyl-6-morpholin-4-yl-4-o-tolyl-nicotinamide in 15 ml tetrahydrofuran, 1.12 ml of a 1 M solution (1.12 mmol) of potassium hexamethyldisilazide in tetrahydrofuran was added at 0° C. After 30 min, 0.16 ml (0.87 mmol) 3,5-bis(trifluoromethyl)benzyl bromide were added dropwise and the reaction mixture was allowed to warm to room temperature over night. Quenching with water was followed by extraction with ethyl acetate. The combined organic extracts were dried with sodium sulfate and concentrated. Column chromatography gave 0.20 g (44%) of the title compound as a white solid.

MS m/e (%): 538 (M+H$^+$, 100).

e) N-(3,5-Bis-trifluoromethyl-benzyl)-N-methyl-6-(4-oxy-morpholin-4-yl)-4-o-tolyl-nicotinamide monohydrate To a solution of 0.40 g (0.74 mmol) N-(3,5-bis-trifluoromethyl-benzyl)-N-methyl-6-morpholin-4-yl-4-o-tolyl-nicotinamide in 4 ml dichloromethane 0.17 g 3-chloroperbenzoic acid (70%; 0.71 mmol) were added at 0° C. After 4 h the reaction mixture was diluted with dichloromethane and washed with 3 portions of saturated sodium carbonate solution. The combined aqueous layers were extracted with dichloromethane. The combined organic extracts were washed with saturated sodium chloride solution, dried with sodium sulfate and concentrated. Column chromatography gave 0.31 g (73%) of the title compound as a white solid.

MS m/e (%): 534 (M+H$^{30}$, 100).

Crystallisation of a portion of 100 mg from a mixture of t-butylmethyl ether and cyclohexane afforded 90 mg of the title compound as white crystals. M.p. 116–117° C.

EXAMPLE 17

N-(3,5-Bis-trifluoromethyl-benzyl)-6-(1,1-dioxo-1$\lambda^6$-4-oxy-thiomorpholin-4-yl)-N-methyl-4-o-tolyl-nicotinamide a) N-(3,5-Bis-trifluoromethyl-benzyl)-N-methyl-6-thiomorpholin-4-yl-4-o-tolyl-nicotinamide The title compound was obtained as a white solid in comparable yields according to the procedures described above for the preparation of 4-{5-[(3,5-bis-trifluoromethyl-benzyl)-methyl-carbamoyl]-4-o-tolyl-pyridin-2-yl}-piperazine-1-carboxylic acid tert-butyl ester using thiomorpholine instead of 1-tert-butoxycarbonyl piperazine in step b) and using N-methyl-6-thiomorpholin-4-yl-4-o-tolyl-nicotinamide instead of 4-(5-methylcarbamoyl-4-o-tolyl-pyridin-2-yl)-piperazine-1-carboxylic acid tert-butyl ester in step c).

MS m/e (%): 554 (M+H$^+$, 100).

b) N-(3,5-Bis-trifluoromethyl-benzyl)-N-methyl-6-(1-oxo-1$\lambda^4$-thiomorpholin-4-yl)-4-o-tolyl-nicotinamide To a solution of 1.24 g (2.24 mmol) N-(3,5-bis-trifluoromethyl-benzyl)-N-methyl-6-thiomorpholin-4-yl-4-o-tolyl-nicotinamide (step a)) in 25 ml methanol were added 689 mg (1.12 mmol) Oxone® at 0° C. After completed addition the reaction mixture was allowed to warm to room temperature and stirred for 1.5 h. Quenching with 5 ml 40% aqueous sodium hydrogen sulfite solution was followed by addition of 6 ml 1N sodium hydroxide solution to adjust the pH to 7–8. The mixture was diluted with 50 ml water and extracted with 3 150-ml portions of dichloromethane. The combined extracts were dried with sodium sulfate and concentrated to give 1.20 g of crude product. Flash chromatography afforded 1.02 g (79.9%) of the title compound as a white solid.

MS m/e (%): 570 (M+H$^+$, 100).

c) N-(3,5-Bis-trifluoromethyl-benzyl)-6-(1,1-dioxo-1$\lambda^6$-thiomorpholin-4-yl)-N-methyl-4-o-tolyl-nicotinamide The parent compound was obtained as a white solid in comparable yield according to the procedure described above (step b)) using N-(3,5-bis-trifluoromethyl-benzyl)-N-methyl-6-(1-oxo-1$\lambda^4$-thiomorpholin-4-yl)-4-o-tolyl-nicotinamide instead of N-(3,5-bis-trifluoromethyl-benzyl)-N-methyl-6-thiomorpholin-4-yl-4-o-tolyl-nicotinamide.

MS m/e (%): 586 (M+H$^+$, 100).

The N-oxide was obtained in accordance with step h) in Example 1.

EXAMPLE 18

N-(3,5-Bis-trifluoromethyl-benzyl)-6-(4-formyl-1-oxy-piperazin-1-yl)-N-methyl-4-o-tolyl-nicotinamide To a mixture of 0.089 ml (1.1 mmol) N,N-dimethylformamide and 38 mg (0.56 mmol) imidazole 0.071 ml (0.56 mmol) trimethylchlorosilane were added dropwise at room temperature. The reaction mixture was cooled to 0° C., and 0.10 g (0.19 mmol) N-(3,5-bis-trifluoromethyl-benzyl)-N-methyl-6-piperazin-1-yl-4-o-tolyl-nicotinamide were added. The ice-water bath was removed and the mixture stirred over night. The reaction was quenched with a mixture of 2 ml 1 N aqueous hydrochloric acid solution and 4 ml water, and the mixture was extracted with ethyl acetate. The combined extracts were dried with sodium sulfate and concentrated. Flash column chromatography afforded 81 mg (82%) of the parent compound as a white solid.

MS m/e (%): 565 (M+H$^+$, 100).

The title compound was obtained in accordance with step h) in Example 1.

EXAMPLE 19

N-Methyl-N-(2-methyl-naphthalen-1-ylmethyl)-6-(4-oxy-morpholin-4-yl)-4-o-tolyl-nicotinamide a) N-Methyl-6-morpholin-4-yl-4-o-tolyl-nicotinamide The title compound was obtained as an off-white solid in comparable yield according to the procedure described above for the preparation of 4-{5-[(3,5-bis-trifluoromethylbenzyl)-methyl-carbamoyl]-4-o-tolyl-pyridin-2-yl}-piperazine-1-carboxylic acid tert-butyl ester (Example 13, step b) using morpholine instead of 1-tert-butoxycarbonyl piperazine.

MS m/e (%): 311 (M$^+$, 63).

b) N-Methyl-N-(2-methyl-naphthalen-1-ylmethyl)-6-morpholin-4-yl-4-o-tolyl-nicotinamide The parent compound was obtained as a white solid in comparable yield according to the procedure described above for the preparation of N-(3,5-bis-trifluoromethylbenzyl)-N-methyl-6-morpholin-4-yl-4-o-tolyl-nicotinamide (Example 16, step d) using 1-chloromethyl-2-methylnaphthalene instead of 3,5-bis-trifluoromethyl-benzyl bromide.

MS m/e (%): 466 (M+H$^+$, 100).

The N-oxide was obtained in accordance with step h) in Example 1.

EXAMPLE 20

N-Methyl-6-(4-oxy-morpholin-4-yl)-N-naphthalen-1-ylmethyl-4-o-tolyl-nicotinamide The parent compound was obtained as a colorless viscous oil in comparable yields according to the procedures described above for the preparation of N-methyl-N-(2-methyl-naphthalen-1-ylmethyl)-6-morpholin-4-yl-4-o-tolyl-nicotinamide (Example 19) using 1-chloromethylnaphthalene instead of 1-chloromethyl-2-methylnaphthalene in step b).

MS m/e (%): 452 (M+H$^+$, 100).

The N-oxide was obtained in accordance with step h) in Example 1.

EXAMPLE 21

N-(2-Methoxy-naphthalen-1-ylmethyl)-N-methyl-6-(4-oxy-morpholin-4-yl)-4-o-tolyl-nicotinamide The parent compound was obtained as a colorless viscous oil in comparable yields according to the procedures described above for the preparation of N-methyl-N-(2-methyl-naphthalen-1-yl-methyl)-6-morpholin-4-yl-4-o-tolyl-nicotinamide (Example 19) using toluene-4-sulfonic acid 2-methoxy-naphthalen-1-yl-methyl ester instead of 1-chloromethyl-2-methylnaphthalene in step b).

MS m/e (%): 482 (M+H$^+$, 100).

The N-oxide was obtained in accordance with step h) in Example 1.

EXAMPLE 22

N-(2-Methoxy-benzyl)-N-methyl-6-(4-oxy-morpholin-4-yl)-4-o-tolyl-nicotinamide

The parent compound was obtained as a colorless viscous oil in comparable yields according to the procedures described above for the preparation of N-methyl-N-(2-methyl-naphthalen-1-yl-methyl)-6-morpholin-4-yl-4-o-tolyl-nicotinamide (Example 19) using 2-methoxy-benzyl chloride instead of 1-chloromethyl-2-methylnaphthalene in step b).

MS m/e (%): 432 (M+H$^+$, 100).

The N-oxide was obtained in accordance with step h) in Example 1.

EXAMPLE 23

N-(5-Chloro-2-methoxy-benzyl)-N-methyl-6-(4-oxy-morpholin-4-yl)-4-o-tolyl-nicotinamide The parent compound was obtained as a white solid in comparable yields according to the procedures described above for the preparation of N-methyl-N-(2-methyl-naphthalen-1-ylmethyl)-6-morpholin-4-yl-4-o-tolyl-nicotinamide (Example 19) using 5-chloro-2-methoxy-benzyl chloride instead of 1-chloromethyl-2-methylnaphthalene in step b).

MS m/e (%): 466 (M+H$^+$, 100).

The N-oxide was obtained in accordance with step h) in Example 1.

EXAMPLE 24

N-(2-Chloro-5-methoxy-benzyl)-N-methyl-6-morpholin-4-yl-4-o-tolyl-nicotinamide

The parent compound was obtained as a white solid in comparable yields according to the procedures described above for the preparation of N-methyl-N-(2-methyl-naphthalen-1-ylmethyl)-6-morpholin-4-yl-4-o-tolyl-nicotinamide (Example 19) using 2-chloro-5-methoxy-benzyl bromide instead of 1-chloromethyl-2-methylnaphthalene in step b).

MS m/e (%): 466 (M+H$^+$, 100).

The N-oxide was obtained in accordance with step h) in Example 1.

EXAMPLE 25

N-Methyl-6-(4-oxy-morpholin-4-yl)-N-pentafluorophenylmethyl-4-o-tolyl-nicotinamide The parent compound was obtained as a white solid in comparable yields according to the procedures described above for the preparation of N-methyl-N-(2-methyl-naphthalen-1-ylmethyl)-6-morpholin-4-yl-4-o-tolyl-nicotinamide (Example 19) using 2,3,4,5,6-pentafluoro-benzyl bromide instead of 1-chloromethyl-2-methylnaphthalene in step b).

MS m/e (%): 492 (M+H$^+$, 100).

The N-oxide was obtained in accordance with step h) in Example 1.

EXAMPLE 26

N-Methyl-6-(4-oxy-morpholin-4-yl)-N-naphthalen-2-ylmethyl-4-o-tolyl-nicotinamide The parent compound was obtained as a white solid in comparable yields according to the procedures described above for the preparation of N-methyl-N-(2-methyl-naphthalen-1-ylmethyl)-6-morpholin-4-yl-4-o-tolyl-nicotinamide (Example 19) using 2-chloromethyl-naphthalene instead of 1-chloromethyl-2-methylnaphthalene in step b).

MS m/e (%): 452 (M+H⁺, 100).

The N-oxide was obtained in accordance with step h) in Example 1.

EXAMPLE 27

N-[2-Methoxy-5-(5-trifluoromethyl-tetrazol-1-yl)-benzyl]-N-methyl-6-(4-oxy-morpholin-4-yl)-4-o-tolyl-nicotinamide The parent compound was obtained as a white solid in comparable yields according to the procedures described above for the preparation of N-methyl-N-(2-methyl-naphthalen-1-ylmethyl)-6-morpholin-4-yl-4-o-tolyl-nicotinamide (Example 19) using toluene-4-sulfonic acid [2-methoxy-5-(5-trifluoromethyl-tetrazol-1-yl)-phenyl]-methyl ester instead of 1-chloromethyl-2-methylnaphthalene in step b).

MS m/e (%): 568 (M+H⁺, 100).

The N-oxide was obtained in accordance with step h) in Example 1.

EXAMPLE 28

N-(1,4-Dimethoxy-naphthalen-2-ylmethyl)-N-methyl-6-(4-oxy-morpholin-4-yl)-4-o-tolyl-nicotinamide The parent compound was obtained as a colorless viscous oil in comparable yields according to the procedures described above for the preparation of N-methyl-N-(2-methyl-naphthalen-1-ylmethyl)-6-morpholin-4-yl-4-o-tolyl-nicotinamide (Example 19) using 2-chloromethyl-1,4-dimethoxy-naphthalene instead of 1-chloromethyl-2-methylnaphthalene in step b).

MS m/e (%): 512 (M+H⁺, 100).

The N-oxide was obtained in accordance with step h) in Example 1.

EXAMPLE 29

5'-[(3,5-Bis-trifluoromethyl-benzyl)-methyl-carbamoyl]-4'-o-tolyl-1-oxy-3,4,5,6-tetrahydro-2H-[1,2']bipyridinyl-4-carboxylic Acid A mixture of 200 mg (0.33 mmol) 5'-[(3,5-bis-trifluoromethyl-benzyl)-methyl-carbamoyl]-4'-o-tolyl-3,4,5,6-tetrahydro-2H-[1,2']bipyridinyl-4-carboxylic acid ethyl ester (Example 14), 10 ml 1 N aqueous sodium hydroxide solution and 10 ml methanol was stirred at room temperature over night. After washing with 2 portions of ethyl acetate the aqueous layer was acidified to pH 4 with 1 N aqueous hydrochloric acid solution. Extraction with dichloromethane, drying with sodium sulfate and flash column chromatography afforded 81 mg (42%) of the parent compound as a white solid.

MS m/e (%): 580 (M+H⁺, 100).

The N-oxide was obtained in accordance with step h) in Example 1.

EXAMPLE A

Tablets of the following composition are manufactured in the usual manner:

| | mg/tablet |
|---|---|
| Prodrug | 5 |
| Lactose | 45 |
| Corn starch | 15 |
| Microcrystalline cellulose | 34 |
| Magnesium stearate | 1 |
| Tablet weight | 100 |

EXAMPLE B

Capsules of the following composition are manufactured:

| | mg/capsule |
|---|---|
| Prodrug | 10 |
| Lactose | 155 |
| Corn starch | 30 |
| Talc | 5 |
| Capsule fill weight | 200 |

The active substance, lactose and corn starch are firstly mixed in a mixer and then in a comminuting machine. The mixture is returned to the mixer, the talc is added thereto and mixed thoroughly. The mixture is filled by machine into hard gelatine capsules.

EXAMPLE C

Suppositories of the following composition are manufactured:

| | mg/supp. |
|---|---|
| Prodrug | 15 |
| Suppository mass | 1285 |
| Total | 1300 |

The suppository mass is melted in a glass or steel vessel, mixed thoroughly and cooled to 45° C. Thereupon, the finely powdered active substance is added thereto and stirred until it has dispersed completely. The mixture is poured into suppository moulds of suitable size, left to cool, the suppositories are then removed from the moulds and packed individually in wax paper or metal foil.

What is claimed is:

1. A compound of the formula

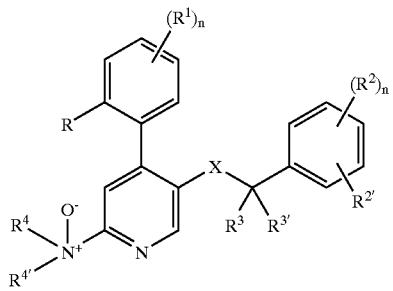

wherein

R is hydrogen, lower alkyl, lower alkoxy, halogen or trifluoromethyl;

$R^1$ is hydrogen or halogen; or

R and $R^1$ when adjacent, together with the ring carbon atoms to which they are attached are —CH=CH—CH=CH—;

$R^2$ and $R^{2'}$ are hydrogen, halogen, trifluoromethyl, lower alkoxy or cyano; or $R^2$ and $R^{2'}$ when adjacent, together with the ring carbons to which they are attached are —CH=CH—CH=CH—, unsubsituted or substituted by one or two substituents selected from lower alkyl or lower alkoxy;

$R^3$ and $R^{3'}$ are hydrogen, lower alkyl or cycloalkyl;

$R^4$ and $R^{4'}$ together with the N-atom to which they are attached form a 5 member nitrogen containing heterocyclic ring of the structure

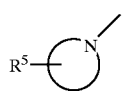

said heterocyclic ring having 0 or 1 additional heteroatoms selected from sulfur, nitrogen and oxygen, said additional hetero-sulfur atom being a sulfonyl moiety;

$R^5$ is hydrogen, hydroxy, lower alkyl, -lower alkoxy, —$(CH_2)_m$OH, —$COOR^3$, —$CON(R^3)_2$, —$N(R^3)CO$-lower alkyl or —$C(O)R^3$;

$R^6$ is lower alkyl;

X is —$C(O)N(R^6)$— —$N(R^6)C(O)$—, —$(CH_2)_mO$—, —$O(CH_2)_m$—;

n is 0, 1, 2, 3 or 4; and m is 1, 2 or 3;

or a pharmaceutically acceptable acid addition salt thereof.

2. The compound of claim 1 wherein R is methyl.

3. The compound of claim 1 wherein R is chloro.

4. The compound of claim 1 wherein $R^2$ and $R^{2'}$ are adjacent and taken together with the rig carbons to which they are attached to form the group —CH=CH—CH=CH—.

5. The compound of claim 1 having the structure

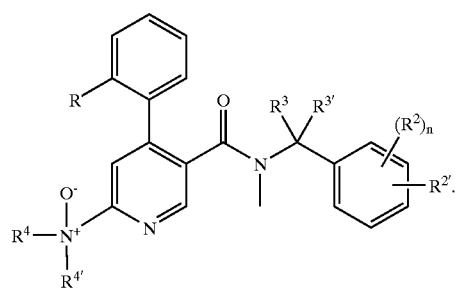

6. The compound of claim 5 wherein R is methyl.

7. The compound of claim 5 wherein R is chloro.

8. The compound of claim 5 wherein $R^2$ and $R^{2'}$ are adjacent and taken together with the rig carbons to which they are attached to form the group —CH=CH—CH=CH—.

9. The compound of claim 1 having the structure

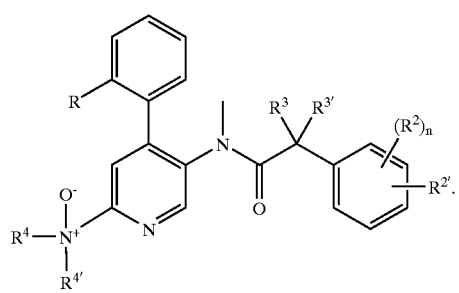

10. The compound of claim 9 wherein R is methyl.

11. The compound of claim 9 wherein R is chloro.

12. The compound of claim 9 wherein $R^2$ and $R^{2'}$ are adjacent and taken together with the rig carbons to which they are attached to form the group —CH=CH—CH=CH—.

13. The compound (RS)-6-[3-(acetyl-methyl-amino)-1-oxo-pyrrolidin-1-yl]-N-(3,5-bis-trifluoromethyl-benzyl)-N-methyl-4-o-tolyl-nicotinamide.

* * * * *

UNITED STATES PATENT AND TRADEMARK OFFICE
CERTIFICATE OF CORRECTION

PATENT NO. : 6,806,370 B2
APPLICATION NO. : 10/645895
DATED : October 19, 2004
INVENTOR(S) : Torsten Hoffmann et al.

It is certified that error appears in the above-identified patent and that said Letters Patent is hereby corrected as shown below:

Title page,
Item [75], Inventors, reads "Torsten D. Hoffmann, Sonia Maria Poli, Patrick Schnider, Andrew Sleight", should read -- Torsten Hoffmann, Sonia Maria Poli, Patrick Schnider, Andrew Sleight --.

Column 33,
Lines 41 and 43, reads "said heterocyclic ring having 0 or 1 additional hetero-atoms selected from sulfur, nitrogen and oxygen, said additional hetero-sulfur atom being a sulfonyl moiety;" should read -- wherein 0 or 1 of the four carbon atoms in said heterocyclic ring is replaced by a hetero-atom selected from sulphur, nitrogen and oxygen, said additional hetero-sulphur atom being a sulphonyl moiety; --.

Column 34,
Lines 4, 25 and 46, read "together with the rig carbons to which", should read -- together with the ring carbons to which --.

Signed and Sealed this

Twentieth Day of June, 2006

JON W. DUDAS
*Director of the United States Patent and Trademark Office*